United States Patent [19]

Bergmeyer et al.

[11] 3,935,071

[45] Jan. 27, 1976

[54] PROCESS FOR THE CONVERSION OF GLUCOSE INTO GLUCONIC ACID

[75] Inventors: Hans Ulrich Bergmeyer; Dieter Jaworek, both of Tutzing, Obb, Germany

[73] Assignee: Boehringer Mannheim G.m.b.H., Mannheim Waldhof, Germany

[22] Filed: Mar. 13, 1973

[21] Appl. No.: 340,775

[30] Foreign Application Priority Data

Mar. 24, 1972  Germany............................ 2214442

[52] U.S. Cl. ...................... 195/32; 195/11; 195/68; 195/109; 195/115
[51] Int. Cl.² ...................... C12D 1/02; C12D 1/06
[58] Field of Search ............. 195/68, 63, 118, 47, 7, 195/11, 65, 115, 32, 109, 103.5 C

[56] References Cited

UNITED STATES PATENTS

| | | | |
|---|---|---|---|
| 3,715,277 | 2/1973 | Dinelli et al. ......................... | 195/68 |
| 3,816,262 | 6/1974 | Monte .......................... | 195/103.5 C |
| 3,830,699 | 8/1974 | Zaborsky .............................. | 195/63 |

FOREIGN PATENTS OR APPLICATIONS

| | | | |
|---|---|---|---|
| 1,294,591 | 11/1972 | United Kingdom................... | 195/68 |
| 923,858 | 4/1963 | United Kingdom................... | 195/11 |

OTHER PUBLICATIONS

Hicks, et al., "The Preparation and Characterization of Lyophilized Polyacrylamide Enzyme Gels for Chemical Analysis," Analytical Chemistry, Vol. 38, No. 6, pp. 726–730, (1966).

*Primary Examiner*—A. Louis Monacell
*Assistant Examiner*—Thomas G. Wiseman
*Attorney, Agent, or Firm*—Burgess, Dinklage & Sprung

[57] ABSTRACT

Glucose is converted into gluconic acid by oxidation with oxygen in aqueous solution, by a process comprising passing a glucose containing aqueous solution over a catalyst which contains glucose oxidase and catalase, bound to an appropriate carrier, in immediate proximity to one another. The process avoids the disadvantage of previous catalytic processes depending on catalysts which rapidly lose their activity and is adapted to large-scale operation.

15 Claims, No Drawings

PROCESS FOR THE CONVERSION OF GLUCOSE INTO GLUCONIC ACID

The present invention is concerned with a process for the conversion of glucose into gluconic acid by the oxidation of glucose in the presence of a catalyst.

The conversion of glucose into gluconic acid is of great interest for many technical purposes. The problem is usually either the separation and removal of glucose from mixtures thereof with other substances, especially with other sugars, such as fructose, or the preparation of gluconic acid. The separation of glucose is a special problem, for example, in the case of sugars which still contain small amounts of glucose, which are extremely difficult to remove. A typical case of this kind is the preparation of fructose for dietetic or pharmaceutical purposes in which it is frequently extremely difficult to reduce the glucose content to the required extent. Similar problems arise in the case of foodstuffs, especially those for diabetics, for example, in the case of fruit juices, beer, wine and the like, in which there is a great need for simple methods for the removal of the glucose present therein.

It is known that glucose can be converted into gluconic acid by oxidation with oxygen in aqueous solution, with the catalytic action of the enzyme glucose oxidase. However, this process is not suitable for large-scale use because glucose oxidase very quickly loses its activity and is also very expensive, so that the use thereof in the necessarily large amounts is not economically feasible.

It is an object of the present invention to overcome the above-mentioned disadvantages and to provide a simple process for the conversion of glucose into gluconic acid which avoids the disadvantages of the known process.

The enzymatic conversion of glucose into gluconic acid by oxidation with oxygen in the presence of glucose oxidase (GOD) takes place according to the following equation:

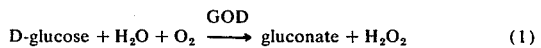

$$\text{D-glucose} + H_2O + O_2 \xrightarrow{\text{GOD}} \text{gluconate} + H_2O_2 \qquad (1)$$

The use of dissolved GOD for the above-mentioned reaction cannot be used on a large scale since the expensive enzyme can only be used for a single reaction batch and, in the case of large-scale batches, a subsequent separation of the enzyme protein is also necessary. Theoretically, these difficulties can admittedly be overcome by using GOD bound to an insoluble carrier. However, it has been found that, in practice, this cannot be carried out because although the carrier-bound GOD can be easily separated, it is inactivated in a very short period of time.

Starting from the assumption that the hydrogen peroxide formed is at least partially responsible for this inactivation, investigations were, therefore, made to overcome this difficulty by the addition of the enzyme catalase to the reaction batch. Catalase decomposes peroxide catalytically, with the formation of oxygen and water, according to the following equation:

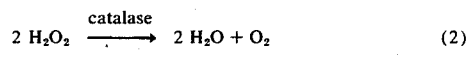

$$2 H_2O_2 \xrightarrow{\text{catalase}} 2 H_2O + O_2 \qquad (2)$$

However, the experiments carried out showed that even in the presence of catalase, the rapid inactivation of GOD cannot be avoided.

The attempt was, therefore, made to use a mixture of carrier-bound GOD with carrier-bound catalase. In order to achieve the most intimate possible contact and thus an immediate removal of the newly formed hydrogen peroxide, each of the enzymes was fixed on finely-divided carrier material and the finely divided carriers obtained then mixed together. However, this also did not overcome the above-mentioned difficulties so that it was assumed that the formation of hydrogen peroxide was not of decisive importance for the ascertained rapid inactivation of the GOD.

Surprisingly, we have now found that the above-mentioned problem can be overcome by using glucose oxidase and catalase bound together on a suitable carrier in immediate proximity with one another. In other words, broadly speaking, a molecule of GOD can be regarded as being present bound to the carrier next to a molecule of catalase. It is to be assumed that, in this way, a kind of cyclic reaction takes place at the molecular level in which the hydrogen peroxide formed by the GOD is again decomposed by the catalase present in the immediate proximity before the hydrogen peroxide can act upon another GOD molecule.

Thus, according to the present invention, there is provided a process for the conversion of glucose into gluconic acid by oxidation with oxygen in aqueous solution, which process comprises passing a glucose-containing aqueous solution over a catalyst which contains glucose oxidase and catalase bound to a carrier and in immediate proximity to one another.

From the above-given equations (1) and (2), it can be seen that, in the case of the process according to the present invention, additional oxygen is necessary only in the case of comparatively high glucose concentrations because the oxygen initially present is always reformed. However, we have found it to be advantageous to add additional oxygen, even when the glucose content of the solution to be treated does not substantially exceed the oxygen content of the solution on a molar basis, the oxygen content being dependent upon the temperature of the solution. In this case, by the addition of oxygen to the solution, a considerable acceleration of the reaction can be brought about. However, the process according to the present invention can also be carried out without additional enrichment with oxygen when the reaction velocity is adjusted to the oxygen content. This can take place by contacting the glucose-containing solution with the carrier-bound enzymes, in the manner of a chromatographic process, in a column with an approximately low flow rate or, for example, by repeatedly recycling the glucose-containing solution over the catalyst.

If the glucose-containing solution is to be enriched with oxygen, this can take place by the addition of pure oxygen or of an agent containing oxygen, especially of a gas such as air. Preferably, the oxygen is added without being admixed with comparatively large amounts of foreign gases.

The process according to the present invention must be carried out at a pH at which the enzyme glucose oxidase and catalase are active. Preferably, a pH value of between 3.5 and 8 is maintained during the reaction, although the enzymes in question still have a certain degree of activity above and below this pH range. Especially good results are achieved in the pH range between 4.5 and 7 and a maximum activity was, in many experiments, measured at pH values between 5 and 5.5. The pH value of the maximum activity also depends upon the origin of the enzymes, for example, whether there is used a catalase from mold fungi, which is preferred, or mammalian liver catalase.

The desired pH can be maintained by the usual chemical methods used for the regulation of pH insofar as the activity of the enzymes is thereby not disadvantageously changed. Good results have been obtained by the addition of lyes, especially of alkaline-reacting compounds of the alkali metals, for example, aqueous solutions of sodium hydroxide, sodium carbonate, potassium hydroxide or the like. Organic bases can also be used in the same way for the adjustment of the pH.

It has proved to be especially expedient to maintain the pH constant within the preferred pH range. This can be achieved, for example, by automatic titration, with the use of a glass electrode and of a pH stat. By means of the measurement results of the pH electrode, the pH stat opens a valve which controls the run off a lye, for example, of an aqueous solution of sodium hydroxide, into the reaction vessel.

The process according to the invention is carried out at a temperature at which the activity of the enzyme has a technically useful value. Preferably, the process is operated at temperatures between 10° and 60°C. At higher temperatures, a noticeable denaturing of the enzyme takes place and at lower temperatures the rate of reaction is too slow. The particularly preferred temperature range is between 25 and 50°C.

The process according to the present invention can be carried out batchwise or continuously. The batchwise embodiment of the process according to the present invention can be carried out particularly simply by adding to a reaction vessel, which contains the glucose-containing aqueous solution, the catalyst to be used according to the process of the present invention, the catalyst then being left in the solution until the desired reaction has taken place. It is expedient to agitate the solution in the usual manner, blowing in of oxygen having proved to be especially advantageous because, on the one hand, it brings about the desired enrichment with oxygen and, on the other hand, results in an agitation of the solution. When the reaction is finished, the catalyst is removed, for example, by centrifuging off, decanting or the like. The catalyst can, without further treatment, be used again and the treated solution itself can be used as such, for example, when it was originally a glucose-containing juice or the like.

According to a further embodiment of the process according to the invention, the reaction takes place in a cycle. This permits an especially simple control of the process. Furthermore, the gluconic acid formed in this way can be separated and thus removed from the equilibrium so that the reaction takes place quickly and quantitatively.

The separation of the gluconic acid formed can be carried out in a conventional manner, for example, by binding to an anion exchanger, conversion into a sparingly soluble salt or other derivative or separation according to other known physical or chemical methods.

In the case of the cyclic embodiment of the process according to the present invention, the gluconic acid can be removed especially well by passage through an anion exchanger. Since, in the continuous reaction in a cycle, the catalyst used according to the present invention is also preferably placed in a column, through which flows the solution to be treated, the process can be carried out by simply connecting together at least two columns in series in such a manner that the solution to be treated first flows through the catalyst to be used according to the present invention and thereafter through the anion exchanger resin.

The catalyst used according to the present invention can be obtained by fixing GOD and catalase, present in an aqueous solution, on to an appropriate carrier. Appropriate carriers and fixing methods are described, for example, in British Pat. Specifications Nos. 1,294,591 and 26556/72. The nature of the carrier used is not critical so long as only GOD and catalase are commonly bound to the carrier in immediate proximity to one another.

The ratio of the activities of GOD to catalase on the carrier is preferably not below 1:1 and, more preferably, the ratio should be 1:10 to more. Very good results have been achieved with activity ratios of up to 1:200. However, it is to be assumed that still higher activity ratios also give outstanding results. A special advantage of the high activity ratios, i.e., of a high bound catalase activity in relation to the GOD activity, is that the oxygen requirement is thereby substantially reduced. This reduction of the oxygen requirement depends upon the immediate reformation of oxygen from the hydrogen peroxide according to equation (2) given above.

In comparison with known chemical processes for the conversion of glucose into gluconic acid and for the separation of glucose from aqueous solutions containing it, the process according to the present invention has the advantage of absolute specificity and extreme simplicity. The process according to the present invention can also be carried out in the presence of very large amounts of chemically similar substances. Thus, it can be used for the removal of comparatively small amounts of glucose in the presence of large amounts of other sugars, for example, of fructose. By means of the process according to the present invention, problems can, thus, be solved which hitherto could not be solved with the previously known chemical and physico-chemical methods. The process according to the present invention is of extremely wide applicability and extends from the removal of glucose from foodstuffs, drinks and the like to the production of glucose-free preparations for the pharmaceutical industry and to the large-scale production of gluconic acid. A special advantage of the use of the process of the present invention for drinks, such as fruit juices, beer, wine and the like, is that the gluconic acid formed can admittedly easily be removed therefrom but it does not have to be removed because it is itself a flavoring which advantageously "rounds off" the flavor of the drinks treated.

The following Examples illustrate the preparation of the carrier-bound GOD-catalase for use in the process according to the present invention:

EXAMPLE A.

50 mg. of a commercially-available GOd preparation with a specific activity of 220 U/mg. were dissolved in 1 ml. 0.5M triethanolamine/hydrochloric acid buffer (pH 8.0), mixed at 30°C with 0.25 ml. acrylic acid 2,3-epoxypropyl ester, while passing in nitrogen, and stirred for about 30 minutes at this temperature. Subsequently, the reaction mixture was cooled to 10°C. Thereafter, 3.0 g. acrylamide, 0.1 g. N,N'-methylene-bis-acrylamide and 300 mg. of an enzyme preparation with a GOD activity of 20 U/mg. and a catalase activity of 260 U/mg. were successively dissolved in 18 ml. distilled water and introduced into the reaction vessel. The polymerization reaction was then initiated by the addition of 50 mg. benzoyl peroxide and 0.5 ml. 5% N,N-dimethylaminopropionitrile solution. When the polymerization was finished (after about 1 hour), the reaction mixture was left to stand for 12–18 hours at 4°C. The polymer formed was then forced through a sieve of mesh size 4 mm., washed and dried.

The specific activity of the carrier-bound enzyme thus obtained was: GOD 281 U/mg. (photometric GOD test according to H.U. Bergmeyer, "Methoden der enzymatischen Analyse", Vol. I, p.416/1970); catalase 185 U/mg. (monometric determination of the liberated oxygen).

In the following, the preparation thus obtained is referred to as GOD-catalase A.

EXAMPLE B.

1.5 g. of an enzyme preparation with a GOD activity of 20 U/mg. and a catalase activity of 260 U/mg., as well as 50 mg. of a catalase of specific activity of 39000 U/mg., were dissolved in 15 ml. distilled water and 7.5 ml. 1M triethanolamine/hydrochloric acid buffer (pH 8.0). 1.25 ml. acrylic acid-2,3-epoxypropyl ester were then added at 30°C., under an atmosphere of nitrogen. Thereafter, the reaction mixture was gently stirred for 30 minutes at this temperature, cooled to 10°C and mixed with 15 g. acrylamide and 0.75 g. N,N'-methylene-bis-acrylamide in 78 ml. distilled water. The polymerization was initiated by the addition of 3 ml. 5% ammonium peroxydisulfate solution and 3 ml. 5% dimethylaminopropionitrile solution. Further working up was carried out in the manner described above in Example A.

The specific activity of the GOD-catalase thus obtained was: GOD 95 U/g. (photometric); catalase 4200 U/g. (photometrically according to H.U. Bergmeyer, "Methoden der enzymatischen Analyse", Vol I, p. 339/1970).

In the following, the preparation thus obtained is referred to as GOD-catalase B.

The following Examples are given for the purpose of illustrating the present invention:

EXAMPLE 1.

Batchwise Carrying Out of the Process.

20 g. (0.11 mol) fructose and 1.1 g. (0.0055 mol) glucose hydrate were dissolved in water to give 200 ml. of solution. The solution was placed in a thermostatically controlled reaction vessel and the temperature was adjusted to 35°C. The reaction vessel was provided with a pH electrode which was connected, via a pH stat, with a burette filled with 0.2N aqueous sodium hydroxide solution. The pH value was maintained constant at 5.5 by automatically adding an appropriate amount of aqueous sodium hydroxide solution to neutralize the gluconic acid formed in the course of the reaction.

Furthermore, the reaction vessel contained an oxygen inlet tube provided with a frit, through which 10 liters oxygen per hour were introduced.

The fructose-glucose solution was now mixed with 250 mg. of a carrier-bound GOD with a specific activity of 300 U/g. At intervals of 50 minutes, the glucose content of the solution was determined. After 100 minutes, 20% of the glucose initially present had been converted into gluconic acid.

In a further experiment, the above-described process was repeated but with the addition of 2 mg. of a catalase with a specific activity of 40000 U/mg. to the solution. After 100 minutes, the glucose conversion was 30% and after 200 minutes was 40%. In the case of still longer reaction times, the GOD was deactivated and could not be reactivated.

In another experiment, the method according to the present invention was used. The procedure was as described for the previous experiments but, instead of using carrier-bound GOD and dissolved catalase, there were added 250 mg. of the above-described GOD-catalase preparation A. After 100 minutes, the conversion of glucose to gluconic acid was about 50% and after 200 minutes was 70%. Inactivation of the enzyme did not occur and, in the case of continued reaction, practically the whole of glucose was converted into gluconic acid.

The above-described process was repeated with the use of the above-described GOD-catalase preparation B. After 100 minutes, about 40% and after 200 minutes 94% of the glucose had been converted into gluconic acid. After 220 minutes, more than 99% of the glucose had been converted into gluconic acid.

The above-described experiments show that, according to the process of the present invention, in spite of substantially lower enzyme activities, very considerably higher conversions of glucose to gluconic acid are achieved. Furthermore, in the process according to the present invention, no noticeable deactivation of the catalyst takes place, whereas in the comparative experiments without the use of catalase and with the use of dissolved catalase, in spite of higher enzyme activities, a rapid and irreversible deactivation of the enzymes took place.

EXAMPLE 2.

Continuous Reaction 1. g of carrier-bound GOD-catalase preparation B was suspended in distilled water and allowed to swell. Subsequently, it was placed in a column of 20 mm. internal diameter and 5 cm. length. Through this column was passed a solution of 50 g. fructose and 2.75 g. glucose hydrate in 500 ml. water, through which air was bubbled at 25° C., the rate of flow of the solution being 1.2 liters per hour. After passage of the reaction solution through the column, the pH value was adjusted to 6.5 with 0.2N aqueous sodium hydroxide solution, oxygen was passed through it and the solution was recycled through the column. Per passage, 100–120 mg. glucose were converted into gluconic acid. After 23 passages, more than 99% of the glucose had been converted into gluconic acid.

EXAMPLE 3

The process of Example 2 was repeated, but an anion exchanger column (acetate-loaded IMAC A 27) was connected in series after the enzyme column and the pH regulation by the addition of an aqueous sodium hydroxide solution was omitted. The solution running off from the exchanger column only contained 0.086% gluconic acid, referred to the fructose content.

EXAMPLE 4

The following experiment shows that the rate of glucose conversion depends upon the ratio of glucose to GOD-catalase catalyst in the solution.

Using the batch process described in Example 1, a solution of 20 g. fructose and 1.1 g. glucose was mixed at 40°C and pH 5.5, while passing in air, with catalyst preparation A according to the present invention. After reaction periods of 100 minutes with different amounts of catalyst, there were obtained the results set out in the following Table:

TABLE

| amount of catalyst (mg.) | glucose reacted after 100 minutes |
|---|---|
| 100 | 24% |
| 250 | 69% |
| 500 | 97% |

It will be understood that the specification and examples are illustrative but not limitative of the present invention and that other embodiments within the spirit and scope of the invention will suggest themselves to those skilled in the art.

What is claimed is:

1. Process for the conversion of glucose into gluconic acid by enzymatic oxidation in the presence of oxygen in aqueous solution, which process comprises passing a glucose-containing aqueous solution over a catalyst comprising an insoluble gel carrier to which is bound a mixture of glucose oxidase and catalase in close side by side proximity.

2. Process as claimed in claim 1, wherein oxygen is passed into the glucose-containing solution.

3. Process as claimed in claim 1, wherein the pH during the reaction is maintained between 3.5 and 8.

4. Process as claimed in claim 3, wherein the pH during the reaction is maintained between 4.7 and 7.

5. Process as claimed in claim 4, wherein the pH during the reaction is maintained between 5 and 5.5.

6. Process as claimed in claim 3, wherein the pH is controlled by the addition of a lye.

7. Process as claimed in claim 3, wherein the pH is controlled by removal of the gluconic acid formed.

8. Process as claimed in claim 1, wherein the reaction is carried out continuously by recycling the treated solution.

9. Process as claimed in claim 8, wherein the catalyst is fixed in a column through which the reactants are passed.

10. Process as claimed in claim 8, wherein the gluconic acid formed is removed from the solution before recycling the solution to the catalyst.

11. Process as claimed in claim 10, wherein the gluconic acid is removed by treatment with an anion exchanger or by conversion into a sparingly soluble derivative thereof.

12. Process as claimed in claim 1, wherein the reaction is carried out at a temperature between 10° and 60°C.

13. Process as claimed in claim 12, wherein the reaction is carried out at a temperature between 25° and 50°C.

14. Process as claimed in claim 1, wherein the ratio of activities of glucose oxidase to catalase is less than 1:1.

15. Process as claimed in claim 14, wherein the ratio of activities of glucose oxidase to catalase is from 1:10 to 1:200.

* * * * *